United States Patent
Driemel (10) Patent No.: US 10,928,467 B2
(45) Date of Patent: Feb. 23, 2021

(54) MAGNETIC RESONANCE COIL APPARATUS HAVING A POSTERIOR COIL UNIT

(71) Applicant: Daniel Driemel, Oederan (DE)

(72) Inventor: Daniel Driemel, Oederan (DE)

(73) Assignee: Siemens Aktiengesellschaft, Munich (DE)

(*) Notice: Subject to any disclaimer, the term of this patent is extended or adjusted under 35 U.S.C. 154(b) by 1145 days.

(21) Appl. No.: 15/005,513

(22) Filed: Jan. 25, 2016

(65) Prior Publication Data
US 2016/0216343 A1     Jul. 28, 2016

(30) Foreign Application Priority Data
Jan. 27, 2015    (DE) .......... 102015201319.7

(51) Int. Cl.
    *G01R 33/34*        (2006.01)
    *A61B 5/055*        (2006.01)

(52) U.S. Cl.
    CPC ...... *G01R 33/34007* (2013.01); *A61B 5/0555* (2013.01); *G01R 33/34084* (2013.01); *G01R 33/34046* (2013.01)

(58) Field of Classification Search
None
See application file for complete search history.

(56) References Cited

U.S. PATENT DOCUMENTS

| | | | |
|---|---|---|---|
| 5,307,806 A | | 5/1994 | Jones |
| 2010/0032545 A1* | | 2/2010 | Bernloehr ............ B63H 20/08 248/640 |
| 2012/0286784 A1 | | 11/2012 | Driemel |
| 2013/0184563 A1* | | 7/2013 | Driemel ........... G01R 33/34007 600/415 |
| 2015/0057528 A1* | | 2/2015 | Driemel ............... A61B 5/0555 600/415 |

FOREIGN PATENT DOCUMENTS

DE     102011075454 A1     11/2012

OTHER PUBLICATIONS

German Office Action for German Application No. 10 2015 201 319.7, dated Oct. 14, 2015, with English Translation.

* cited by examiner

*Primary Examiner* — Pascal M Bui Pho
*Assistant Examiner* — Marjan Saboktakin
(74) *Attorney, Agent, or Firm* — Lempia Summerfield Katz LLC (57) ABSTRACT

A magnetic resonance coil apparatus has a posterior coil unit. The magnetic resonance coil apparatus having a posterior coil unit includes a base unit, a tilting unit and a force transmission unit. The tilting unit, which includes at least one coupling element, is arranged on the base unit such that the tilting unit can tilt with respect to the base unit. For each coupling element of the tilting unit, the base unit includes at least one corresponding coupling element. The coupling state between the at least one coupling element of the tilting unit and the at least one corresponding coupling element of the base unit can be changed by actuating the force transmission unit.

19 Claims, 7 Drawing Sheets

MAGNETIC RESONANCE COIL APPARATUS HAVING A POSTERIOR COIL UNIT

RELATED CASE

This application claims the benefit of DE 102015201319.7, filed on Jan. 27, 2015, which is hereby incorporated by reference in its entirety.

FIELD

The present embodiments relate to a magnetic resonance coil apparatus having a posterior coil unit and to a method for producing same.

In magnetic resonance imaging (MRI), local magnetic resonance coil apparatuses, known as local coils or surface coils, are normally used to capture images having a high signal-to-noise ratio (SNR). For this purpose, the local magnetic resonance coil apparatuses are positioned on a subregion to be examined of a subject under examination, in particular of a patient, for the magnetic resonance examination. These apparatuses are antenna systems, which are mounted in the immediate vicinity on (anterior) or under (posterior) the subject under examination. In an MRI measurement, electromagnetically excited nuclei induce in the local coil a voltage, which is usually amplified by a low-noise preamplifier and normally routed via cable to the electronic receiver.

Local coils may have various designs depending on the body region of the patient for which an image is meant to be generated. Types of coil include ankle coils, wrist coils, knee coils, chest coils, shoulder coils, head coils, neck coils, and head/neck coils. For specific magnetic resonance examinations, it may be useful to tilt the relevant local magnetic resonance coil apparatus with respect to a supporting surface on which the patient is supported for the magnetic resonance examination.

SUMMARY AND DESCRIPTION

The scope of the present invention is defined solely by the appended claims and is not affected to any degree by the statements within this summary.

A magnetic resonance coil apparatus allows particularly convenient adjustment to suit the subject under examination.

The magnetic resonance coil apparatus having a posterior coil unit includes a base unit, a tilting unit and a force transmission unit. The tilting unit, which includes at least one coupling element, is arranged on the base unit such that the tilting unit may tilt with respect to the base unit. For each coupling element of the tilting unit, the base unit includes at least one corresponding coupling element. The coupling state between the at least one coupling element of the tilting unit and the at least one corresponding coupling element of the base unit may be changed by actuating the force transmission unit.

The magnetic resonance coil apparatus preferably includes an anterior coil unit and a posterior coil unit, said anterior coil unit and said posterior coil unit enclosing a receiving zone for accommodating a subregion of the subject under examination, for instance a head of the patient and/or a knee of the patient. In this case, the posterior coil unit lies by a side facing away from the receiving zone on a patient support apparatus, which is designed to be movable in order to support the patient inside a magnetic resonance machine. The side of the posterior coil unit facing away from the patient receiving zone is incorporated by the base unit, the position of which with respect to the patient support apparatus, in particular of a supporting surface of the patient support apparatus, is preferably maintained during the entire magnetic resonance examination. In addition, the base unit may also be mounted on the supporting surface of the patient support apparatus.

It is particularly advantageous if the posterior coil unit also includes a tilting mechanism, for instance at least one pivot and/or hinge, by which the tilting unit is arranged and/or mounted on the base unit such that the tilting unit may tilt with respect to the base unit. Coupling elements may be used to lock a tilt position of the tilting unit with respect to the base unit. In this case, at least one coupling element is preferably mounted on the tilting unit, and for each coupling element of the tilting unit, at least one corresponding coupling element is mounted on the base unit. An interaction of the at least one coupling element of the tilting unit and of the at least one corresponding coupling element of the base unit has the advantageous effect that the relative position between tilting unit and base unit may be fixed or released. The fixed state and the released state correspond to two possible coupling states between the at least one coupling element of the tilting unit and the at least one corresponding coupling element of the base unit.

This interaction typically causes the at least one coupling element of the tilting unit to interact directly and physically, in particular mechanically, with the at least one corresponding coupling element of the base unit. The manner of this interaction may be such that a detachable form-fit is made between the coupling elements, in particular said coupling elements interlock. For example, the at least one coupling element of the tilting unit has one or more protruding or outwards-pointing contours, for instance one or more teeth or pegs, which reaches and/or engages into a possible locating contour, for instance a recess or inwards pointing orifice such as a notch and/or a hole, of the at least one corresponding coupling element. It is also possible that the at least one corresponding coupling element includes a plurality of locating contours, which are arranged at different positions, preferably about a tilt axis or along a direction of tilt, so that it is possible to adjust the tilt position of the tilting unit with respect to the base unit to a different setting. Of course complementary embodiments are also possible, in which the at least one coupling element of the tilting unit includes one or more locating contours and the at least one corresponding coupling element of the base unit includes one or more protruding contours.

Moreover, other interaction mechanisms are possible between the coupling elements, for instance a force-locking or frictional connection of the coupling elements. Thus, for instance, both the at least one coupling element of the tilting unit and the at least one corresponding coupling element of the base unit may each have at least one friction surface, which is coupled when pressed against another, or in other words constitute a detachable connection. The force for producing the pressing force or contact pressure may be produced by one or more springs, for example.

A force, in particular a muscular force, by which the coupling state between the at least one coupling element of the tilting unit and the at least one corresponding coupling element of the base unit may be changed, may preferably be imparted by actuating the force transmission unit. This may mean in particular that a potential locking of the tilting unit may be established and removed again by actuating the force transmission unit. The force may cause a movement, in particular a rotation, of the force transmission unit, by which the at least one coupling element of the tilting unit and the at least one corresponding coupling element of the base unit may be moved relative to one another. For example, the apparatus according to one embodiment may be designed such that, by a force imparted by the force transmission unit, any one or more outwards-pointing contours of the tilting unit may be moved into or out of any one or more inwards-pointing contours of the base unit.

Changing a setting of the tilt position of the tilting unit with respect to the base unit also changes an orientation and/or position of the receiving zone of the magnetic resonance coil apparatus with respect to the patient support apparatus, in particular with respect to the supporting surface of the patient support apparatus. In particular, this changes a position and/or orientation of the entire magnetic resonance coil apparatus, except the base unit, with respect to the patient support apparatus, in particular with respect to the supporting surface of the patient support apparatus. The base unit is preferably oriented parallel to the supporting surface of the patient support apparatus.

The adjustability of the tilt position of the tilting unit with respect to the base unit may advantageously increase patient comfort, for instance by it being possible to adjust the position of the local magnetic resonance coil apparatus in particular to suit an anatomy of the patient. If, for instance, the magnetic resonance coil apparatus is formed by a head coil apparatus, a neck coil apparatus and/or a combined head/neck coil apparatus, then in particular for patients who have pathological conditions affecting the cervical spine, for instance Bekhterev's disease, torticollis etc., it is possible to achieve greater comfort in supporting the patient by virtue of the tilt function of the magnetic resonance coil apparatus.

The force transmission unit is preferably mounted on the tilting unit. This advantageously allows the force transmission unit to be integrated in the magnetic resonance coil apparatus. It is thereby easier to combine any movements to change the coupling state with movements to change the tilt position. Thus, it is possible that the coupling state may be changed, for instance, by applying a force to the force transmission unit in a first direction (e.g., by releasing a possible locking state), and the tilt position is adjusted by applying a force to the force transmission unit in a second direction that differs from the first direction.

In another embodiment, the force transmission unit includes at least one operating control. This operating control may be used to apply a force to the force transmission unit, in particular to alter the coupling state between the at least one coupling element of the tilting unit and the at least one corresponding coupling element of the base unit.

The at least one operating control may be designed in the form of a handle, a knob, a pushbutton, or a button, for example. It is preferably shaped, for instance by adapting the geometric shape of the operating control to the anatomy of a human hand, such that any operating staff may perform an ergonomic operation. The force transmission unit may be actuated, for example, by pressing or pushing or pulling the at least one operating control. It is also possible that the operating control is integrated in the magnetic resonance coil apparatus in such a way that the options for actuating and/or moving said control are determined by its geometry and/or the geometry of any components surrounding said control (e.g., such that the operating control can move back and forth in just one direction only over a limited distance).

It is possible that the operating control is rigidly connected, in particular monolithically, to the force transmission unit. Other types of arrangement are also possible, however, for instance by a joint.

In a preferred variant, the force transmission unit is mounted on the tilting unit such that the force transmission unit may rotate about a rotational axis. In this variant, both the at least one coupling element and the at least one operating control are arranged on the force transmission unit, and the ratio of a distance from the at least one coupling element to the rotational axis with respect to a distance from the at least one operating control to the rotational axis is less than 2. This ratio lies in particular between 0 and 1.6, preferably between 0.2 and 1.2 and more preferably from 0.3 to 1. Particularly advantageous, in particular free-moving, embodiments of the adjustment mechanism may be achieved using these values.

Since the operating control and coupling element are normally non-punctiform objects, it is the convention when defining the distance of the element concerned from the rotational axis to use the point at which the force of the operating staff is applied to the at least one operating control or at which the force transferred by the force transmission unit is applied to the at least one coupling element.

For rotation through a given angle, the distance between the at least one coupling element and the rotational axis typically determines the travel distance of the at least one coupling element. Depending on the shape of the coupling element, for example a length of a latching tooth or a depth of a corresponding recess, a certain minimum travel distance, and hence a certain distance between the at least one coupling element and the rotational axis, may be necessary to effect a change in a coupling state.

For a given force applied to the operating control, the moment of force produced by said force increases proportionately with the distance of the rotational axis from the operating control. Thus owing to this lever action, as large a distance as possible initially appears advantageous so that any operating staff need to apply minimum possible force to actuate the operating control. On the other hand, the travel to actuate the operating control increases with increasing distance, which in turn may prove disadvantageous because the increasing distance is laborious for any operating staff. Taking into account the space usually available in magnetic resonance coil apparatuses, the specified ratios constitute advantageous compromises.

In one embodiment, the base unit preferably includes two or more coupling elements. In this embodiment, at least one coupling element is arranged on each of two opposite sides of the tilting unit.

The tilting unit usually has an extension parallel to the direction of a potential rotational axis about which the force transmission unit may be rotatably mounted. A notional center plane may be defined and/or imagined. The notional center plane is orientated at right angles to this rotational axis and lies centrally inside the extension of the tilting unit. At least one coupling element may be arranged on the tilting unit on each side of this center plane.

By using two or more coupling elements, the coupling mechanism may have a more robust and/or sturdy design. In particular for an arrangement on two opposite sides, the coupling force may be distributed more evenly over the tilting unit and/or base unit.

In another embodiment of the magnetic resonance coil apparatus, the force transmission unit includes two or more operating controls. In this embodiment, at least one operating control is arranged on each of two opposite sides of the force transmission unit.

The force transmission unit usually has an extension parallel to the direction of a potential rotational axis about which the force transmission unit may be rotatably mounted.

A notional center plane may be defined, which is orientated at right angles to this rotational axis and lies centrally inside the extension of the force transmission unit. At least one operating control may be arranged on each side of this center plane. It is particularly advantageous for one operating control to be mounted at each end of the force transmission unit parallel to the potential rotational axis.

In addition, a patient support apparatus usually has at least two sides from which any operating staff may perform measurement preparations. Some of the measurement preparations may be adjusting the tilt positions of the magnetic resonance coil apparatus. The accessibility of the operating controls for any operating staff may be increased if at least one operating control is located on each of these two sides of the patient support apparatus.

In a particularly preferred variant, the coupling state between all the coupling elements of the tilting unit and all the corresponding coupling elements of the base unit may be changed simultaneously by actuating the force transmission unit. The force transmission unit may be actuated by one or more operating controls. For instance, if one operating control is arranged at each end of the base unit parallel to the potential rotational axis, then it is possible to change the coupling state of all the coupling elements at once by applying force to the force transmission unit using just one operating control, so that in particular there is no need for two-handed operation. Since one operating control may be arranged on each side, the accessibility of the operating control also advantageously does not depend on which side of the patient support apparatus any operating staff are currently located.

If, for example, the tilting mechanism used provides latching positions for locking the tilt position, then locking and/or unlocking actions by any operating staff may be required. For ergonomic reasons, a mechanism is desirable that may be operated with just one hand by any operating staff. For reasons of space, it is often not possible to implement an arrangement that would otherwise be conceivable, in which just one locking and/or unlocking operating control is positioned centrally so that any operating staff would be able to reach potentially from either side of the magnetic resonance coil apparatus or of the patient support apparatus. One operating control may be arranged on each side, for instance, so that a central arrangement of just one operating control can be avoided.

In addition, interaction of any operating staff over the head of a potential patient that may be unpleasant to the patient may be avoided because it is not necessary to actuate an operating control positioned centrally or even on the opposite side.

In another embodiment, the force transmission unit includes a connecting element that has an internal cavity. Various coupling elements and/or various operating controls may be connected to one another by the connecting element. The cavity allows weight to be saved while achieving high rigidity.

In particular, the connecting element may be tubular in form. In addition, the force transmission unit may be mounted such that the force transmission unit may rotate about the center axis of the tube. The tubular shape ensures high torsional stiffness and allows an injection molding process to be used for manufacture, avoiding material build-ups.

In an advantageous development, it is proposed that the force transmission unit includes at least one stiffening member.

Such a stiffening member may have a planar design and may be arranged on a possible connecting element. In particular, the stiffening surface may have a flat design, and the plane that encompasses the flat stiffening surface may contain a possible center axis of a possible connecting element.

It is also possible that a stiffening member makes the connection of an operating control to a coupling element more robust.

Stiffening members may increase the torsional stiffness of the force transmission unit. If a plurality of coupling elements are used, the stiffening members may reduce twisting between the points at which the force transmission unit applies a force to the coupling elements. This may have an advantageous effect particularly when these force-application points are mounted far apart from one another on opposite sides of the force transmission unit.

Furthermore, at least one of the stiffening members may be strengthened by ribs. In particular, such ribs may be arranged in diamond formations and/or on a possible planar stiffening member. This advantageously further increases the torsional stiffness.

In another variant of the magnetic resonance coil apparatus, the force transmission unit has a monolithic part. This can mean in particular that the force transmission unit is made of one piece and/or constitutes a unit that may not be taken apart without being destroyed. Ideally, the force transmission unit integrates as a single part all the functional elements such as stiffening members, for instance, so that a plurality of separate parts may be dispensed with in manufacture and assembly.

It is also proposed that the magnetic resonance coil apparatus is a head coil apparatus or a neck coil apparatus or a head/neck coil apparatus. In this case, it is possible to achieve greater comfort in supporting the patient by virtue of the tilt function of the magnetic resonance coil apparatus. Comfort is particularly advantageous for patients who have pathological conditions affecting the cervical spine, for instance Bekhterev's disease, torticollis etc. As an alternative, the magnetic resonance coil apparatus may be formed by any magnetic resonance coil apparatuses that a person skilled in the art considers practical.

Furthermore, a method for producing a force transmission unit is proposed. The production method is an injection molding technique. An injection molding technique in particular is especially suitable for producing the force transmission unit from, for example, fiber-reinforced or spherical-particle reinforced plastics, including plastics such as polyamide (PA), polycarbonate (PC), polybutylene terephthalate (PBT), polyphenylene sulfide (PPS) for instance.

Owing to the alternating electromagnetic fields used for spatial encoding and for exciting the resonances, parts for magnetic resonance coil apparatuses for MRI examinations are often made from glass-fiber reinforced plastics, which are neither electrically conducting nor ferromagnetic and, thanks to a high density, have a high strength, in order to avoid interactions with the alternating electromagnetic fields and hence to make the component MR compatible. In addition, the strength suppresses interference from vibrations of the components.

BRIEF DESCRIPTION OF THE DRAWINGS

Further advantages, features and details of the invention appear in the exemplary embodiment described below and with reference to the drawings.

DETAILED DESCRIPTION

Figure 1:
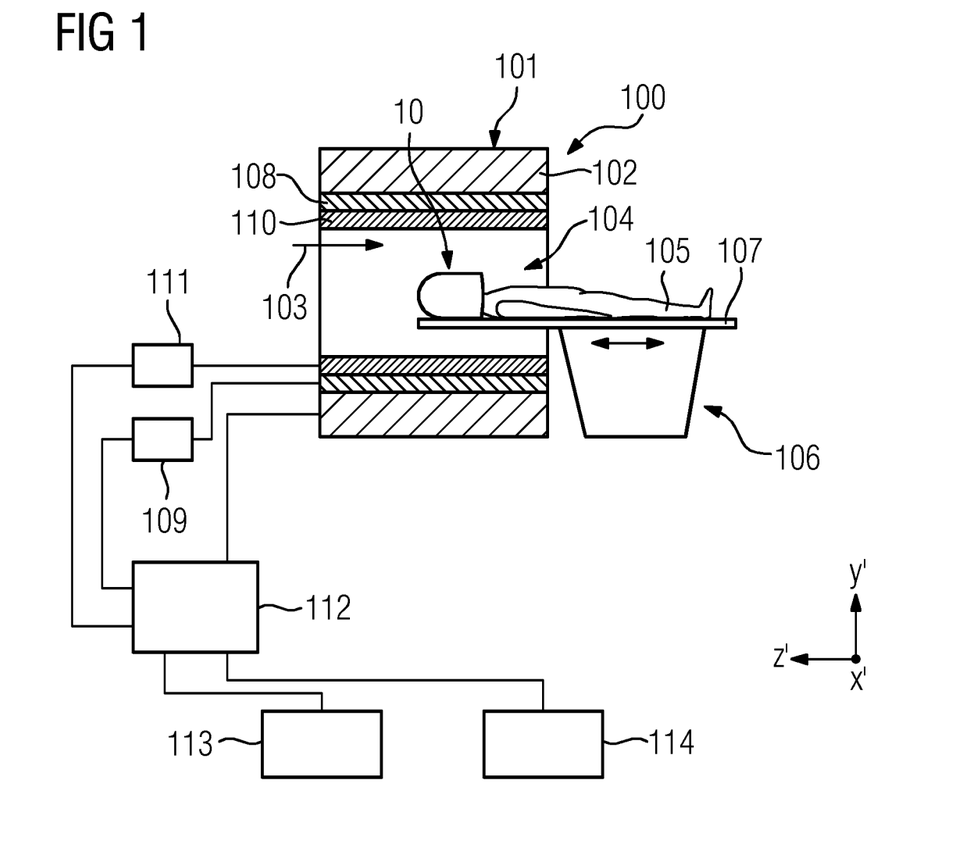
FIG. 1 is a schematic diagram of one embodiment of a magnetic resonance coil apparatus.

FIG. 1 shows schematically a magnetic resonance machine 100 in a lateral cross-sectional view. The magnetic resonance machine 100 includes a magnet unit 101 containing a superconducting main magnet 102 for generating a powerful and in particular constant main magnetic field 103. The magnetic resonance machine 100 also includes a patient receiving zone 104 for accommodating a patient 105. In the present exemplary embodiment, the patient receiving zone 104 is shaped as a cylinder and is enclosed in a circumferential direction cylindrically by the magnet unit 101. In principle, however, it is always possible for the patient receiving zone 104 to have a different design. The patient 105 may be moved in the z'-direction into the patient receiving zone 104 by a patient support apparatus 106 of the magnetic resonance machine 100.

The magnet unit 101 further includes a gradient coil unit 108 for generating magnetic-field gradients, which are used for spatial encoding during imaging. The gradient coil unit 108 is controlled by a gradient control unit 109 of the magnetic resonance machine 100. The magnet unit 101 further includes an RF antenna unit 110 and an RF antenna control unit 111 for exciting a polarization that establishes itself in the main magnetic field 103 generated by the main magnet 102. The RF antenna unit 110 is controlled by the RF antenna control unit 111 and radiates RF magnetic resonance sequences into an examination space, which is largely formed by a patient receiving zone 104 of the magnetic resonance machine 100.

The magnetic resonance machine 100 includes a system control unit 112 for controlling the main magnet 102, the gradient control unit 109, and the RF antenna control unit 111. The system control unit 112 includes a processor unit and memory unit, which are not shown in greater detail. In addition, the system control unit 112 includes software and/or a computer program required for operation. The system control unit 112 centrally controls the magnetic resonance apparatus, for instance implementing a predetermined imaging gradient echo sequence. In addition, the system control unit 112 includes an analysis unit (not shown in greater detail) for analyzing image data. Control data such as imaging parameters, for instance, and reconstructed magnetic resonance images may be displayed to an operator on a display unit 113, for example on at least one monitor, of the magnetic resonance machine 100. In addition, the magnetic resonance machine 100 includes an input unit 114, which may be used by an operator to enter data and/or parameters during a measurement process.

For a magnetic resonance examination on the patient 105, what are known as local magnetic resonance coil apparatuses 10 are positioned on the patient 105 for the purpose of detecting magnetic resonance signals. In the present exemplary embodiment, the magnetic resonance coil apparatus 10 is formed by a head coil apparatus. The head coil apparatus is designed so that the head coil apparatus may tilt, for which purpose a supporting surface of the head coil apparatus 3 is tilted with respect to a supporting surface 107 of the patient support apparatus 106. Tilting may increase comfort in supporting the patient 105, for instance for patients 105 who have pathological conditions affecting the cervical spine, for instance Bekhterev's disease, torticollis etc.

FIGS. 2 to 8 show partial views of a posterior coil unit 99 of the magnetic resonance coil apparatus 10 according to one embodiment formed by the head coil apparatus. Alternatively, the magnetic resonance coil apparatus 10 may also be formed by other magnetic resonance coil apparatuses 10 that a person skilled in the art considers practical, for instance by a neck coil apparatus, a head/neck coil apparatus, a knee coil apparatus, an ankle coil apparatus, a wrist coil apparatus, a chest coil apparatus, or a shoulder coil apparatus.

Figure 2:
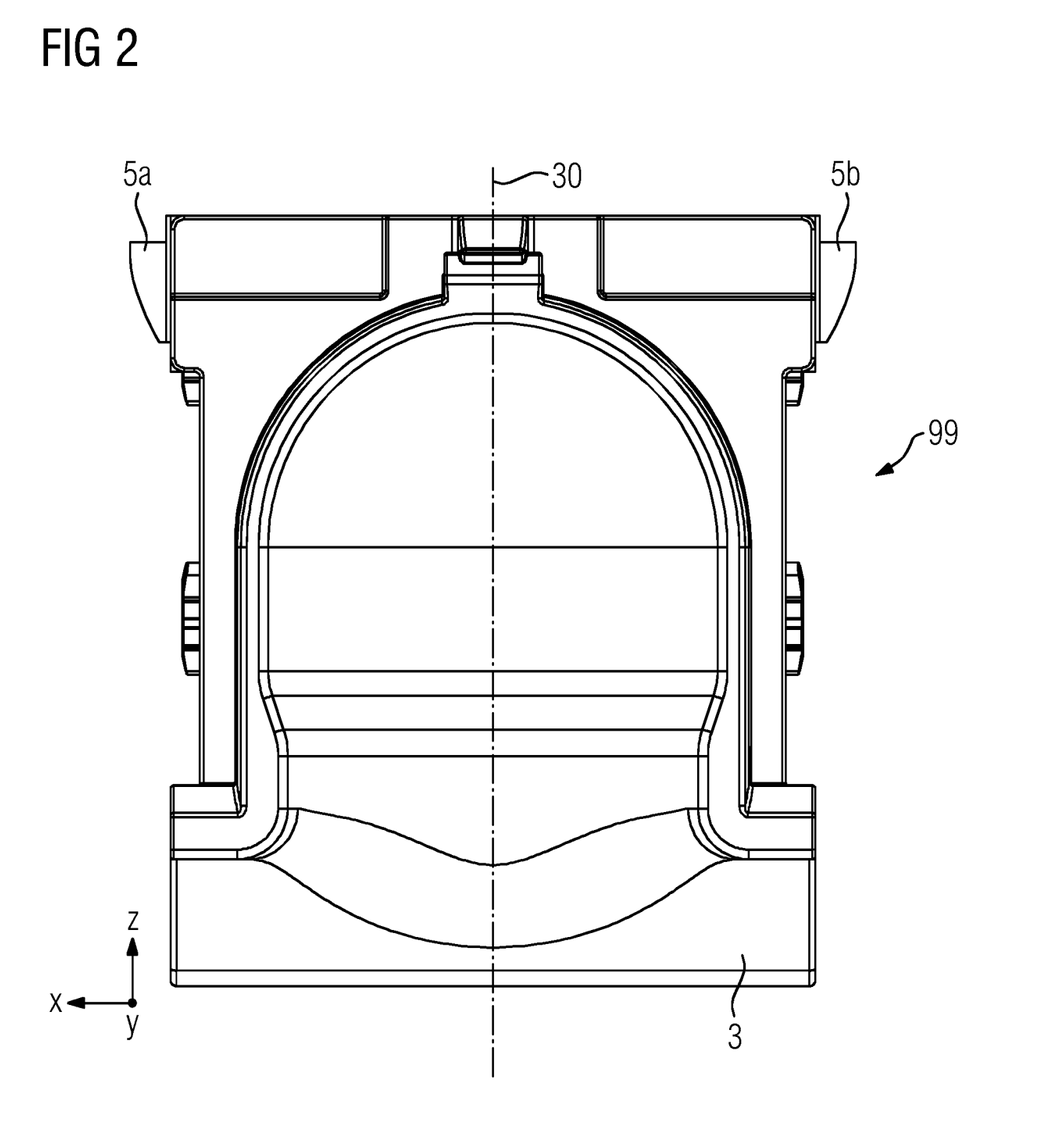
FIG. 2 is a plan view of a posterior coil unit, according to one embodiment.

FIG. 2 shows a plan view of a posterior coil unit 99. This unit 99 includes a head support unit 3, on which the head of a patient 105 may be supported, and two operating controls 5a, 5b, which protrude parallel to the x-axis on both sides. Embodiments in which the number of operating controls differs from this embodiment are also possible. Like the typical anatomy of a human head, the posterior coil unit 99 has a plane of symmetry 30, which lies parallel to the y and z coordinate axes. This plane of symmetry 30 divides the posterior coil unit 99 into two sides, where the operating control 5a is arranged on the one side, and the operating control 5b on the opposite side. The magnetic resonance coil apparatus 10 is usually arranged inside a magnetic resonance machine 100 during a measurement in such a way that the coordinate systems of FIG. 1 and FIG. 2 coincide (i.e., the x'-axis of FIG. 1 is parallel to the x-axis of FIG. 2, etc). Thus the operating controls 5a, 5b are each allocated to one of the two sides of the patient support apparatus 106 that lie opposite in a direction parallel to the x-axis. Thanks to the resultant accessibility, it is possible for any operating staff to operate comfortably the operating control 5a from one side of the patient support apparatus 106 and to operate comfortably the operating control 5b from the other side.

Figure 3:
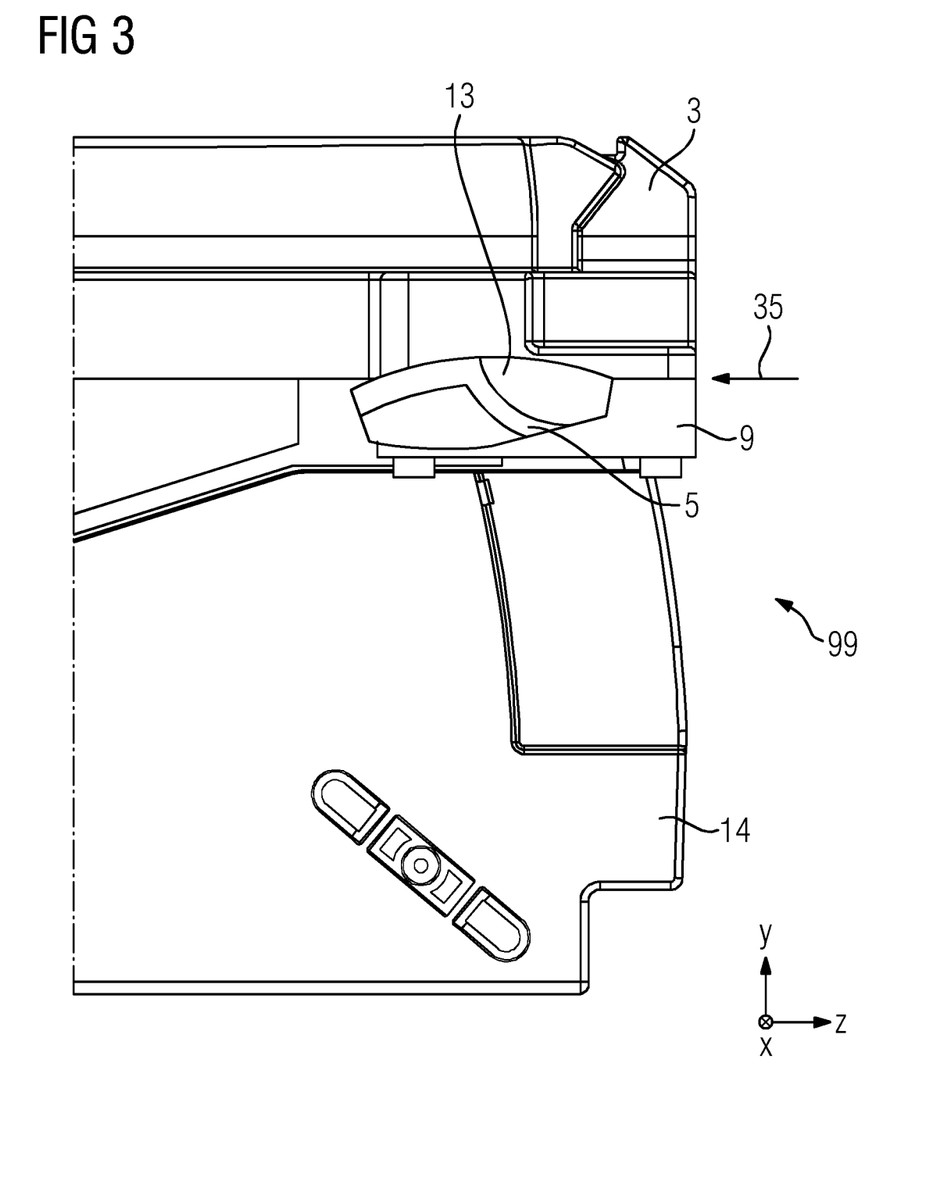
FIG. 3 is a side view of a posterior coil unit, according to one embodiment.
Figure 4:
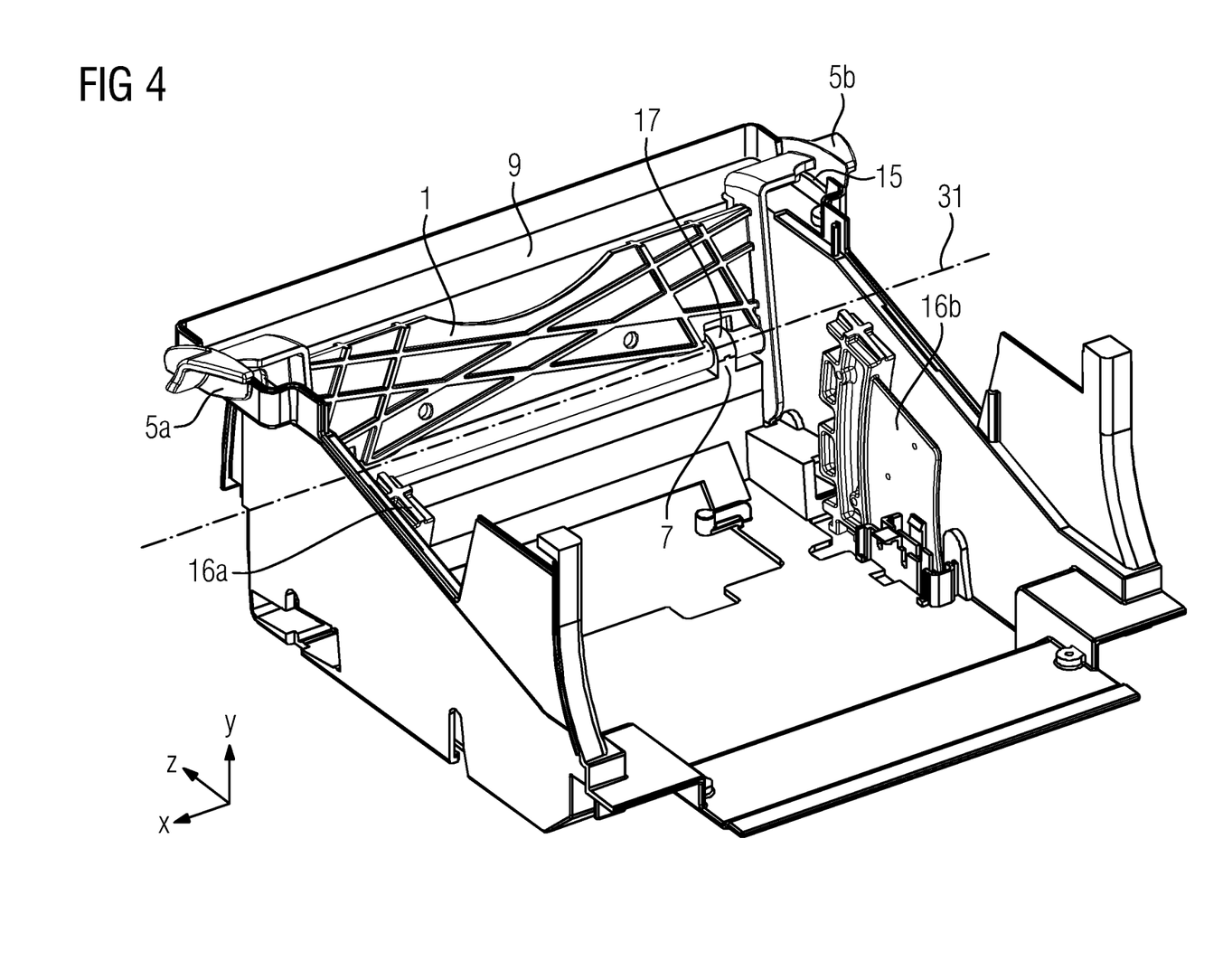
FIG. 4 is a perspective partial view of a posterior coil unit, according to one embodiment.

FIG. 3 shows a side view of the posterior coil unit 99. The head support unit 3 is rigidly connected to the tilting unit 9 so that the head support unit 3 may be tilted together with the tilting unit 9. The operating unit 5 includes a covering surface 13, which ensures that the aperture 15 lying behind and shown in FIG. 4 is covered in every possible angular position of the operating unit 5. Apart from reasons of visual appearance, this covering surface 13 has the advantage that the covering surface 13 protects the interior of the magnetic resonance coil apparatus 10, for instance from dirt. A side wall of the base unit 14 is also shown, which is designed to move with respect to the tilting unit 9.

FIG. 4 shows the interior of the tilting unit 9. A force transmission unit 1 is mounted by pivots 7 on the tilting unit 9 such that the force transmission unit 1 may rotate about a rotational axis 31 parallel to the x-direction. The force transmission unit 1 is unable to move with respect to the tilting unit 9 axially, parallel to the rotational axis 30, by virtue of a rib 8 (shown in greater detail in FIG. 6), which is mounted on the force transmission unit 1. A pivot 7 includes an annular groove on the tilting unit 9 and a clasp 17, which also has an annular groove. These two grooves form a common circumferential groove, which holds the rib 8 in a form-fit. In addition, FIG. 4 shows two corresponding coupling elements 16a, 16b of the base unit. In FIG. 4, the corresponding coupling element 16a is largely concealed by a side wall of the tilting unit 9.

Figure 5:
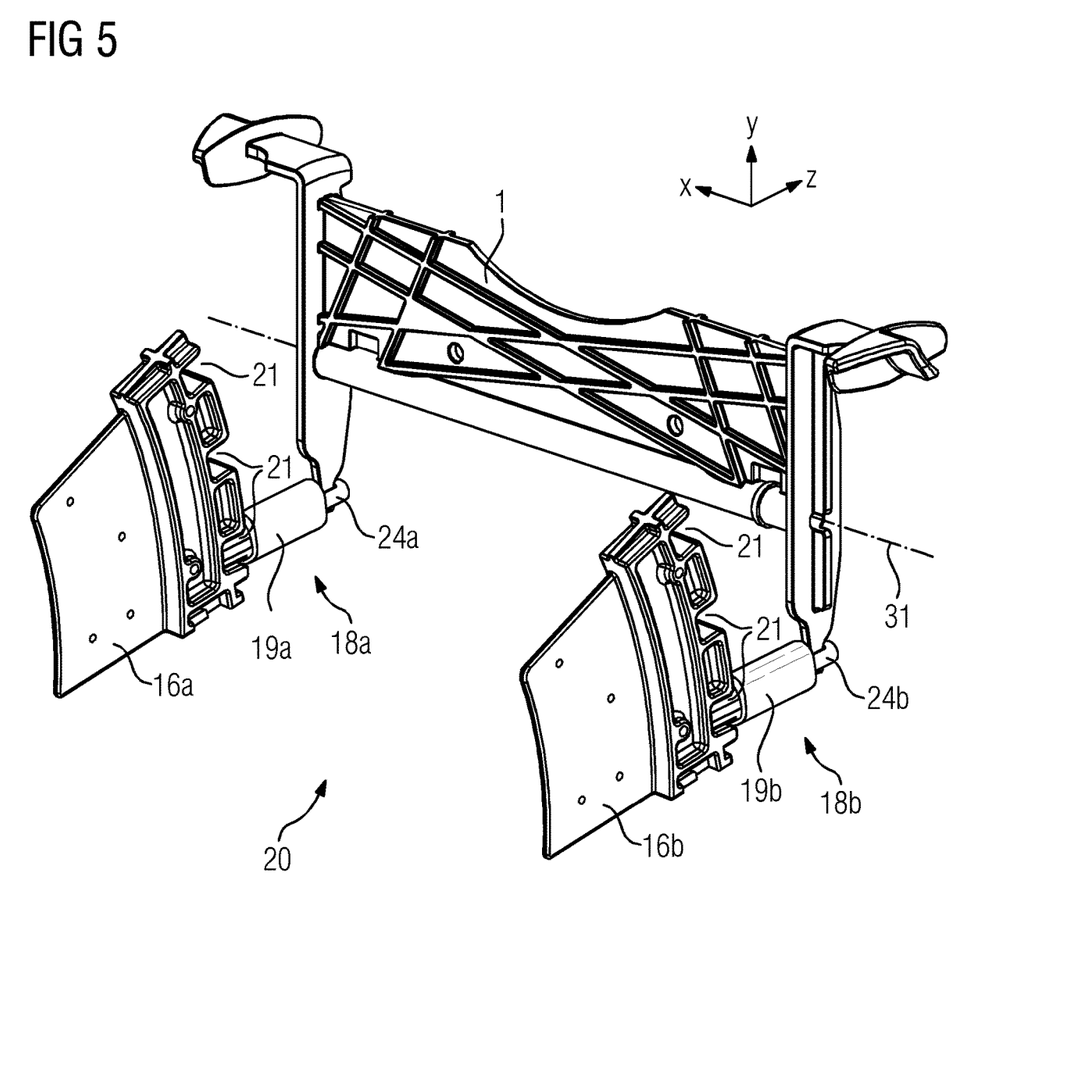
FIG. 5 is a perspective partial view of a posterior coil unit, according to one embodiment.
Figure 7:
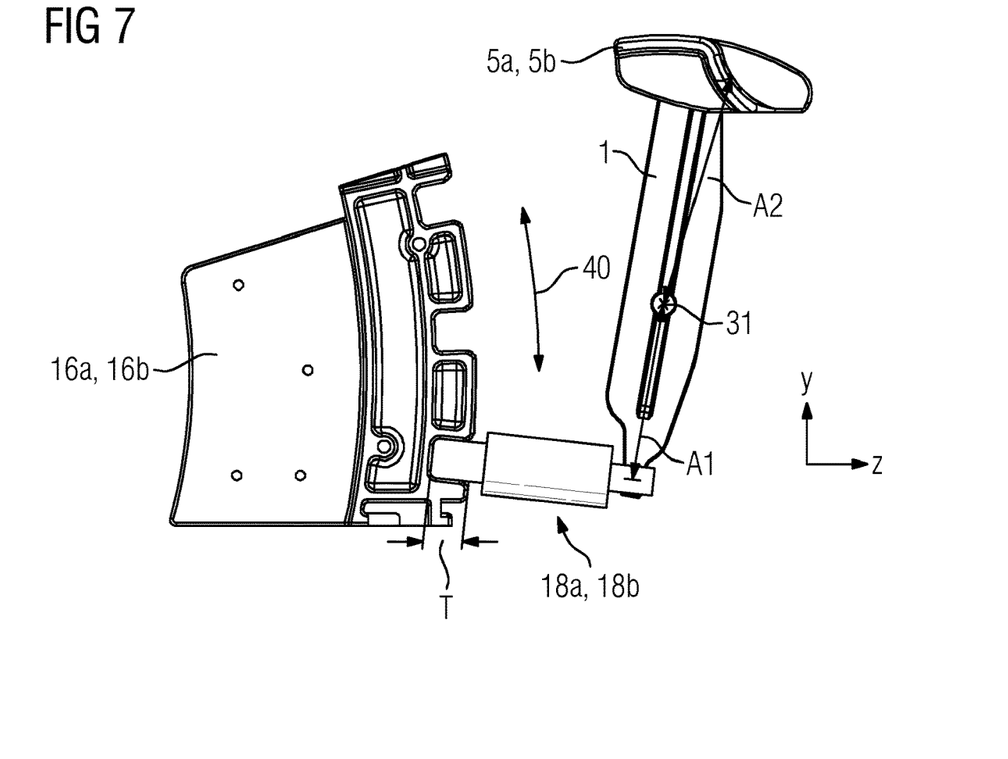
FIG. 7 is a side view of one embodiment of a latching mechanism in a locked coupling state.
Figure 8:
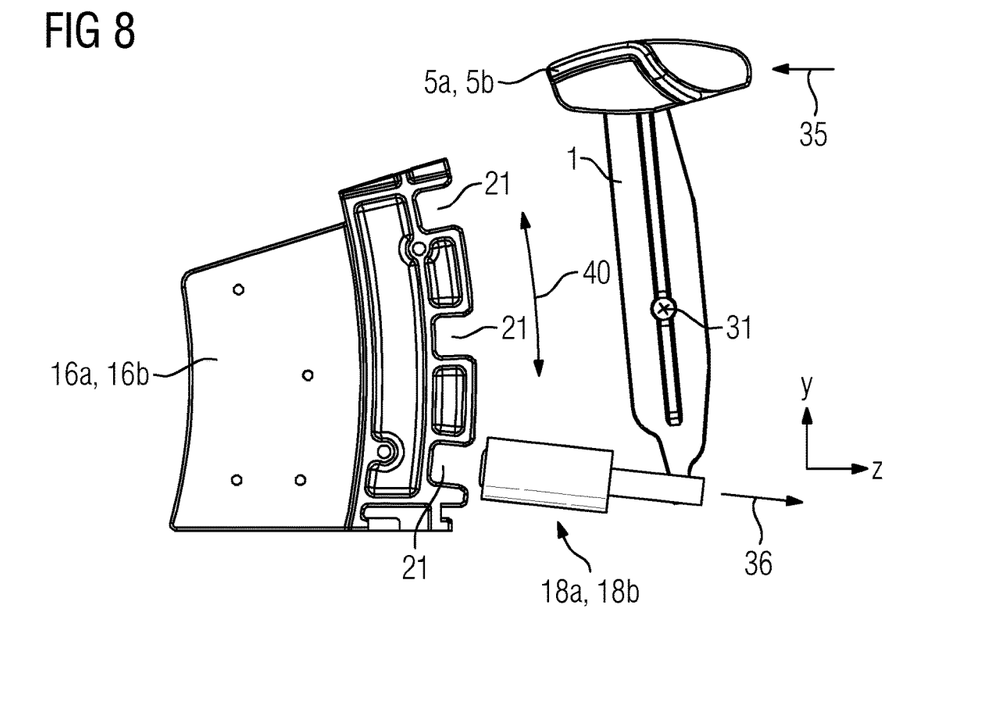
FIG. 8 is a side view of one embodiment of a latching mechanism in an unlocked coupling state.

FIG. 5 illustrates the tilting mechanism. Two coupling elements 18a, 18b are arranged via the force transmission unit 1 on the tilting unit 9, each of which coupling elements includes a guide element 19a, 19b and a coupling pin 24a, 24b. Each coupling pin 24a, 24b is movably mounted in a corresponding guide element 19a, 19b. The base unit 14 includes, for each of these coupling elements 18a, 18b of the tilting unit 9, a corresponding coupling element 16a, 16b. Between the coupling elements 16a, 16b is a region 20, which may be used, for instance, as an installation space for electronic circuitry of the magnetic resonance coil apparatus. Each of the corresponding coupling elements 16a, 16b has three locating contours 21, which are arranged along a direction of tilt 40, as shown in FIG. 7 and FIG. 8. A different number of locating contours is obviously also possible as an alternative to the example shown.

These locating contours 21 constitute latching positions in which two coupling elements 18a, 18b, here embodied as a peg or stud 24a, 24b, may be engaged. FIG. 5 shows, like FIG. 7, a coupling state between the two coupling elements 18a, 18b of the tilting unit 9 and the two corresponding coupling elements 16a, 16b of the base unit 14, in which state the tilting unit 9 is locked or fixed to the base unit 14. This connected or locked coupling state may be changed by actuating the force transmission unit 1 by manually pressing the operating controls 5a, 5b, for instance by any operating staff, and transferred to a released or unlocked coupling state. The aperture 15 here limits the possible distance through which the operating controls 5a, 5b can be moved.

As shown in FIG. 8, such pressing 35 in a direction that has a component in the negative z-direction results in the force transmission unit 1 rotating about the rotational axis 31, with the result that the two coupling elements 18a, 18b are pulled out of the locating contours 21 in a direction that has a component in the positive z-direction. The aperture 15 is advantageously designed to be of a size such that the two coupling elements 18a, 18b may be pulled fully out of the locating contours 21. The fact that the force transmission unit 1 connects the operating controls 5a, 5b and coupling elements 18a, 18b rigidly to one another, of which there are two in this example, means that it is possible by actuating just one of the two operating controls 5a, 5b, in particular by single-handed operation, to change simultaneously the coupling state between all the coupling elements 18a, 18b of the tilting unit and all the corresponding coupling elements 16a, 16b of the base unit. Hence any operating staff can lock and unlock the latching mechanism regardless of which side of the patient support apparatus 106 they are located, and for this purpose in particular need not reach entirely or partly across the head of the patient 105. In the unlocked state, the tilting unit 14 may be tilted in a direction of tilt 40, possibly about a tilt axis (not shown here), and relocked for instance in a different latching position 21 by pressing at least one of the two operating controls 5a, 5b in a substantially positive z-direction. By a spring (not shown here), it is also possible that the force transmission unit 1 is preloaded such that the force for moving the operating controls 5a, 5b is provided by the spring in a substantially positive z-direction so that to unlock, any operating staff merely need to release the operating controls 5a, 5b.

FIG. 7 also shows a distance A1 of the at least one coupling element 18a, 18b from the rotational axis 31, and a distance A2 of the at least one operating control 5a, 5b from the rotational axis 31. The ratio V=A1/A2 is approximately 0.8 in the example shown. This ratio is advantageously less than 2. This ratio lies in particular between 0 and 1.6, preferably between 0.2 and 1.2 and more preferably from 0.3 to 1. Particularly advantageous, in particular free-moving, embodiments of the adjustment mechanism may be achieved using these values.

The common origin for the distances A1 and A2 is the rotational axis or pivot point 31. The other endpoint of the distance 42 is the point at which the force of the operating staff is applied to the operating control 5a, 5b. The other endpoint of the distance 42 is the point at which the force transferred by the force transmission unit is applied to the coupling element 18a, 18b. As the present example shows, the vectors, which may be formed by the described origins and endpoints, need not be parallel to one another.

The minimum distance through which the coupling element 18a, 18b is moved for unlocking equals the depth T of the notch 21 of the corresponding coupling element 16a, 16b. The minimum angle α through which the force transmission unit 1 is rotated may be evaluated from α=arctan (T/A1). Likewise, the minimum travel distance W of the operating control 5a, 5b may be evaluated from W=T/V. Hence, the smaller the ratio V, the larger the travel distance W. The larger the travel distance W, the more precisely any operating staff may set the travel of the coupling elements 18a, 18b.

Usually a minimum force F1 is necessary to be applied to the coupling element 18a, 18b to perform the locking and unlocking. This corresponds to a moment of force M=A1× F1. The moment of force produced by actuating the operating control 5a, 5b is calculated from M=A2×F2, where F2 is the applied force, which is applied to the force transmission unit by any operating staff. Substituting for the moment of force M results in F2=F1/V. Hence, the smaller the ratio V, the smaller is the necessary force that any operating staff must apply.

On the other hand, as the ratio V gets smaller, the travel distance W=T/V to actuate the operating control increases, which in turn may prove disadvantageous because this is laborious for any operating staff. Taking into account the space usually available in magnetic resonance coil apparatuses, the specified ratios constitute advantageous compromises.

Figure 6:
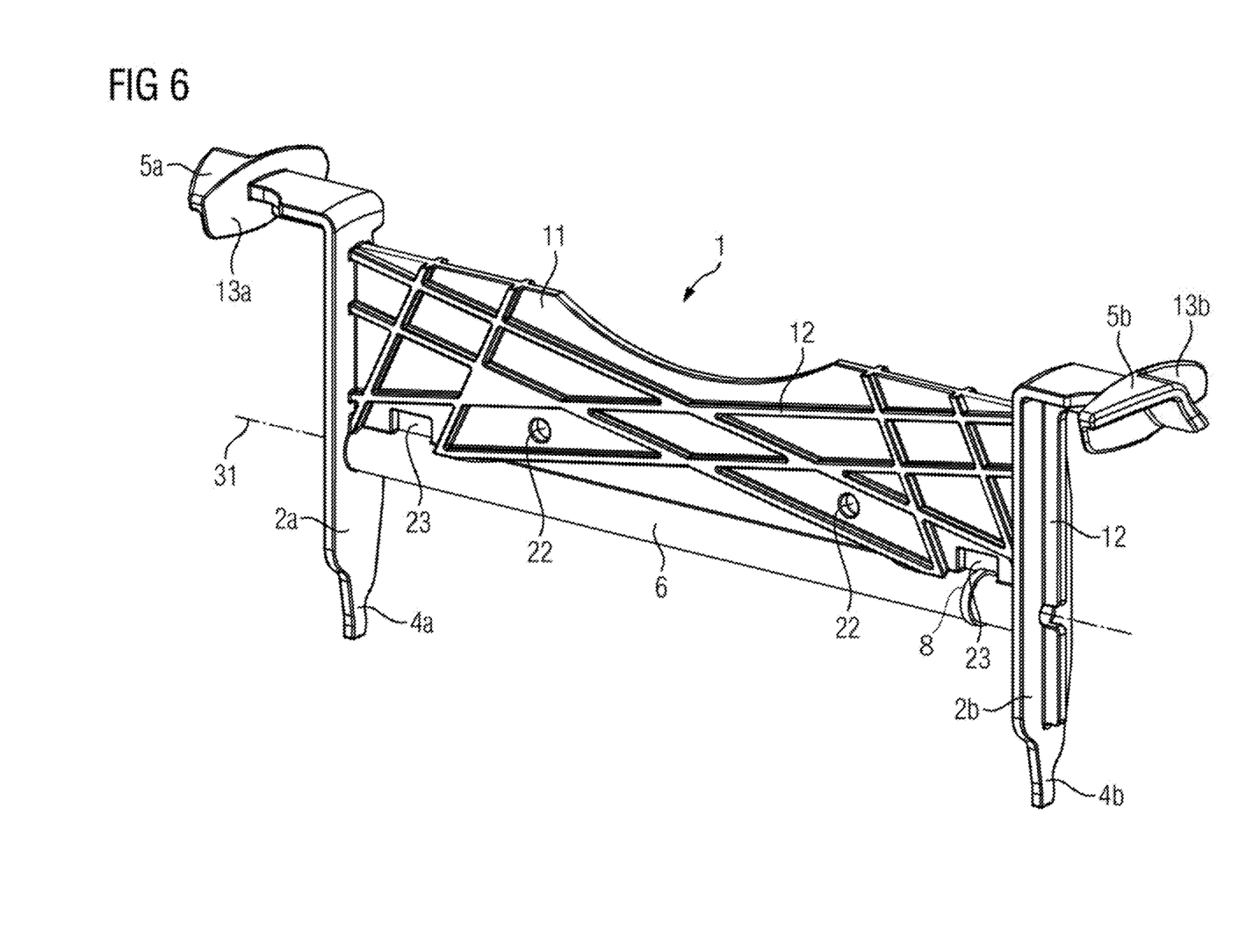
FIG. 6 is a perspective view of one embodiment of a force transmission unit.

FIG. 6 shows in greater detail an exemplary embodiment of the force transmission unit 1 consisting of one monolithic single part. At each end of the force transmission unit 1 with respect to the rotational axis 31 is arranged a side panel 2a, 2b, each including a drive peg 4a, 4b. These drive pegs 4a, 4b are designed to move the coupling elements 18a, 18b on actuation of the force transmission unit 1. In addition, the coupling elements 18a, 18b are arranged on these drive pegs 4a, 4b. The side panels 2a, 2b are connected to one another by a connecting element 6, which is embodied as a tube (i.e. it has an internal cavity) to increase the torsional stiffness. Its tubular shape also means that the connecting element 6 may be made at low cost as an injection-molded part. The force transmission unit 1 is arranged in the magnetic resonance apparatus 10 such that the force transmission unit 1 may rotate about the center axis of the tube 31, In order to increase the torsional stiffness, the force transmission unit 1 also includes a stiffening member, which here is in the form of an intermediate wall 11 that is arranged on the connecting element 6 and connects the side panels 2a, 2b. The intermediate wall 11 and the side panels 2a, 2b are equipped with ribs 12, in the case of the intermediate wall 11 as diagonal ribs on both sides, in order to increase the torsional stiffness further. Of course the stiffening members may also be arranged or shaped differently from that in the example shown. In addition, the exemplary embodiment shown has two holes 22, which can be used as possible cable feedthroughs, and two recesses 23, in which to locate the clasps 17 of the pivots 7.

The invention has been described above with reference to preferred exemplary embodiments. It shall be understood, however, that the invention is not restricted to the specific embodiment of the illustrated exemplary embodiments but in fact a person skilled in the art can derive variations from the description without departing from the essential fundamental idea of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A magnetic resonance coil apparatus comprising:
a posterior coil unit and an anterior coil unit, wherein the posterior coil unit and the anterior coil unit enclose a receiving zone for accommodating a subregion of a subject under examination,
wherein the posterior coil unit of the magnetic resonance coil apparatus comprises:
a base unit,
a tilting unit comprising two or more couplers, the tilting unit arranged on the base unit such that the tilting unit is operable to tilt with respect to the base unit, and
a force transmission member,
wherein two of the two or more couplers of the tilting unit are arranged on opposite sides of the tilting unit,
wherein for each coupler of the tilting unit, the base unit comprises at least one corresponding coupler,
wherein the force transmission member is configured to move the two or more couplers of the tilting unit between a locked state and an unlocked state via a first application of force to the force transmission member in a first direction,
wherein the force transmission member is configured to move the tilting unit to change a tilt position when in the unlocked state via a second application of force to the force transmission member in a second direction, wherein the second direction differs from the first direction,
wherein, in the locked state, the two or more couplers of the tilting unit are coupled with the at least one corresponding coupler of the base unit and the tilting unit is locked to the base unit, and
wherein, in the unlocked state, the two or more couplers of the tilting unit are not coupled with the at least one corresponding coupler of the base unit and the tilting unit is unlocked from the base unit.

2. The magnetic resonance coil apparatus as claimed in claim 1, wherein the force transmission member is mounted on the tilting unit.

3. The magnetic resonance coil apparatus as claimed in claim 1, wherein the force transmission member comprises at least one operating control.

4. The magnetic resonance coil apparatus as claimed in claim 1, wherein the force transmission member comprises a connecting element having an internal cavity.

5. The magnetic resonance coil apparatus as claimed in claim 4, wherein the connecting element is tubular, and the force transmission member is mounted such that the force transmission member is operable to rotate about a center axis of the connecting element.

6. The magnetic resonance coil apparatus as claimed in claim 1, wherein the force transmission member comprises at least one stiffening member.

7. The magnetic resonance coil apparatus as claimed in claim 6, wherein at least one of the stiffening member is strengthened by ribs.

8. The magnetic resonance coil apparatus as claimed in claim 1, wherein the force transmission member is a monolithic part.

9. The magnetic resonance coil apparatus as claimed in claim 1, wherein the magnetic resonance coil apparatus comprises a head coil apparatus, a neck coil apparatus, or a head/neck coil apparatus.

10. The magnetic resonance coil apparatus as claim in claim 1 wherein the force transmission member comprises an injection molded part.

11. The magnetic resonance coil apparatus as claimed in claim 2, wherein the force transmission member comprises at least one operating control.

12. The magnetic resonance coil apparatus as claimed in claim 11, wherein the force transmission member comprises two or more operating controls, and
wherein at least one of the operating control is arranged on each side of two opposite sides of the force transmission member.

13. The magnetic resonance coil apparatus as claimed in claim 12, wherein the force transmission member comprises a connecting element having an internal cavity.

14. The magnetic resonance coil apparatus as claimed in claim 13, wherein the force transmission member comprises at least one stiffening member.

15. The magnetic resonance coil apparatus as claimed in claim 3, wherein the force transmission member is configured to be actuated by pressing, pushing, pulling, or a combination thereof of the at least one operating control.

16. A magnetic resonance coil apparatus comprising:
a posterior coil unit and an anterior coil unit, wherein the posterior coil unit and the anterior coil unit enclose a receiving zone for accommodating a subregion of a subject under examination,
wherein the posterior coil unit of the magnetic resonance coil apparatus comprises:
a base unit,
a tilting unit comprising two or more couplers, the tilting unit arranged on the base unit such that the tilting unit is operable to tilt with respect to the base unit, and
a force transmission member comprising at least one operating control, wherein the force transmission member is mounted on the tilting unit such that the force transmission member is operable to rotate about a rotational axis, wherein two of the two or more couplers of the tilting unit are arranged on opposite sides of the tilting unit, wherein for each coupler of the tilting unit, the base unit comprises at least one corresponding coupler, wherein the force transmission member is configured to move the two or more couplers of the tilting unit between a locked state and an unlocked state via an actuation of the force transmission member, wherein, in the locked state, the two or more couplers of the tilting unit are coupled with the at least one corresponding coupler of the base unit and the tilting unit is locked to the base unit, wherein, in the unlocked state, the two or more couplers of the tilting unit are not coupled with the at least one corresponding coupler of the base unit and the tilting unit is unlocked from the base unit, wherein the two or more couplers of the tilting unit and the at least one operating control are arranged on the force transmission member, and wherein a ratio of a distance from the two or more couplers to the rotational axis with respect to a distance from the at least one operating control to the rotational axis is less than 2.

17. A magnetic resonance coil apparatus comprising:

a posterior coil unit and an anterior coil unit, wherein the posterior coil unit and the anterior coil unit enclose a receiving zone for accommodating a subregion of a subject under examination, wherein the posterior coil unit of the magnetic resonance coil apparatus comprises:

a base unit, a tilting unit comprising two or more couplers, the tilting unit arranged on the base unit such that the tilting unit is operable to tilt with respect to the base unit, and a force transmission member, wherein two of the two or more couplers of the tilting unit are arranged on opposite sides of the tilting unit, wherein for each coupler of the tilting unit, the base unit comprises at least one corresponding coupler, wherein the force transmission member is configured to move the two or more couplers of the tilting unit between a locked state and an unlocked state via an actuation of the force transmission member, wherein, in the locked state, the two or more couplers of the tilting unit are coupled with the at least one corresponding coupler of the base unit and the tilting unit is locked to the base unit, and wherein, in the unlocked state, the two or more couplers of the tilting unit are not coupled with the at least one corresponding coupler of the base unit and the tilting unit is unlocked from the base unit, wherein the magnetic resonance coil apparatus is configured to be positioned on a support surface that supports the subject under examination extending along a longitudinal axis, wherein the force transmission member has a first end and a second, opposite end, wherein the force transmission member extends along a rotational axis from the first end to the second end, and wherein the rotational axis is perpendicular to the longitudinal axis, wherein the force transmission member comprises two operating controls, and wherein a first operating control of the two operating controls is arranged on the first end of the force transmission member and a second operating control of the two operating controls is arranged on the second end of the force transmission member opposite the first end such that the first operating control is positioned on one side of the support surface and the second operating control is positioned on a second, opposite side of the support surface.

18. The magnetic resonance coil apparatus as claimed in claim 17, wherein the force transmission member is configured to be moved by a single operating control of the two operating controls positioned on opposite ends of the force transmission member such that an operator is configured to move the force transmission member from either side of the support surface by actuating the operating control closest to the operator and without having to reach entirely or partially over the subregion of the subject under examination to actuate the opposite operating control.

19. The magnetic resonance coil apparatus as claimed in claim 18, wherein each operating control of the two operating controls comprises a handle.

\* \* \* \* \*